(12) United States Patent
Armstrong et al.

(10) Patent No.: US 9,790,251 B2
(45) Date of Patent: Oct. 17, 2017

(54) CONVERSION OF CELLULOSE INTO SIMPLE SUGARS

(71) Applicant: Baker Hughes Incorporated, Houston, TX (US)

(72) Inventors: Charles David Armstrong, Tomball, TX (US); Stanley Gunawan, The Woodlands, TX (US); Lawrence N. Kremer, The Woodlands, TX (US)

(73) Assignee: Baker Hughes Incorporated, Houston, TX (US)

( * ) Notice: Subject to any disclaimer, the term of this patent is extended or adjusted under 35 U.S.C. 154(b) by 385 days.

(21) Appl. No.: 14/339,566

(22) Filed: Jul. 24, 2014

(65) Prior Publication Data

US 2015/0051391 A1    Feb. 19, 2015

Related U.S. Application Data

(60) Provisional application No. 61/865,283, filed on Aug. 13, 2013.

(51) Int. Cl.
*C13K 1/02* (2006.01)
*C07H 3/02* (2006.01)
*C07H 1/00* (2006.01)

(52) U.S. Cl.
CPC ............ *C07H 3/02* (2013.01); *C07H 1/00* (2013.01); *C13K 1/02* (2013.01)

(58) Field of Classification Search
CPC ............ C13K 1/02; C07H 1/00; C07H 3/02
See application file for complete search history.

(56) References Cited

U.S. PATENT DOCUMENTS

| | | | | |
|---|---|---|---|---|
| 4,174,676 A | * | 11/1979 | Wulff | C23C 14/246 118/688 |
| 4,250,306 A | * | 2/1981 | Lask | A61L 15/28 536/85 |
| 4,410,694 A | | 10/1983 | Nakayama et al. | |
| 5,441,109 A | * | 8/1995 | Gupta | C09K 8/605 166/300 |

OTHER PUBLICATIONS

Shigemasa et al, Dissolution of Cellulose in Dimethyl Sulfoxide, Effect of Thiamine Hydrochloride, Polymer Journal, vol. 22, No. 12, pp. 1101-1103 (1990).*
Yamanaka et al, Determination of Thiamine in Dried Yeast by High-Performance Liquid Chromatography Using a Clean Up Column of CM-Cellulose, Journal of Chromotography A, 726, pp. 237-240, (1996).*
Rickards et al, "Enzymatic Breaker System for Nondamaging Removal of Cellulose-Based Blocking Gels", SPE Produiction Operations Symposium, Mar. 21-23, Oklahoma City Oklahoma, (1993).*
Z. Congying, "Ruthenium Porphyrins and Dirhodium (II, II) Carboxylates Catalyzed Ylide-Mediated Cycloadditions and Carbenoid Transfer", Abstract, HKU Scholars Hub, The University of Hong Kong, Jan. 2004.

* cited by examiner

*Primary Examiner* — David M Brunsman
(74) *Attorney, Agent, or Firm* — Mossman, Kumar & Tyler, P.C.

(57) ABSTRACT

Cellulose may be converted into simple sugars such as glucose by contacting the cellulose with a compound effective to catalytically cleave the ether bonds of the cellulose. The compound may be a vitamin, a porphyrin, flavins, pyridoxal-containing molecules, and/or a compound containing at least one ylide functional group. The cellulose may be carboxymethyl cellulose (CMC), which may be made by reacting cellulose with chloroacetic acid and a base such as NaOH. The compound may be vitamins (B1, B2, B6, or B12), phosphonium ylides, sulfonium ylides, sulfoxonium ylides, carbonyl ylides, oxonium ylides, asomethine ylides, iminium ylides, halonium ylides, and combinations thereof. The free glucose may be used for fermentation, converted to a biofuel and for other applications.

17 Claims, 1 Drawing Sheet

CONVERSION OF CELLULOSE INTO SIMPLE SUGARS

CROSS-REFERENCE TO RELATED APPLICATION

This application claims the benefit of U.S. Provisional Patent Application No. 61/865,283 filed Aug. 13, 2013, incorporated herein by reference in its entirety.

TECHNICAL FIELD

The present invention relates to methods for converting cellulose into simple sugars, and more particularly relates in one non-limiting embodiment to converting cellulose into simple sugars, such as glucose, by catalytically cleaving the ether bonds.

TECHNICAL BACKGROUND

Cellulose is a polysaccharide compound with the formula $(C_6H_{10}O_5)_n$ consisting of a linear chain of several hundred to over ten thousand β(1→4) linked D-glucose units joined by an oxygen (ether) linkage to form long molecular chains that are essentially linear. Cellulose may be decomposed to glucose by the enzyme cellulase, and, in an alternative process, it may be hydrolyzed to glucose. The degree of polymerization for cellulose may range from about 1000 for wood pulp to about 3500 for cotton fiber, giving a molecular weight from about 160,000 to about 560,000. Being naturally formed by plants, cellulose is the most abundant organic polymer on Earth. Conversion of cellulose from crops into biofuels such as ethanol, has been developed as a fuel source process alternative to traditional sources such as refining oil and gas. Glucose sugar may also be used for fermentation.

The efficient hydrolysis of cellulose to form fermentable sugar will open up vast natural resources for the production of biofuels. Cellulose consists of crystalline and amorphous regions. By treating it with a strong acid, the amorphous regions can be broken up to produce crystalline cellulose. The slow step in converting cellulose to fuel is the hydrolysis. It is particularly slow for crystalline cellulose since crystalline cellulose is not soluble in water.

U.S. Pat. No. 4,250,306 relates to a process for preparing swellable cross-linked carboxyalkylcelluloses by reacting cellulose, a carboxyalkylating etherifying agent, and a cross-linking agent in an aqueous alkaline medium, comprising effecting alkalizing, etherifying, and cross-linking simultaneously in one reaction step using fibers, textile sheet materials containing these fibers, or sheet materials of other kinds, having a base of cellulose hydrate or of natural cellulose, by contacting said fibers or sheet materials with an ample quantity of an aqueous alkaline reaction mixture, removing part of the reaction mixture from the fibers or sheet materials contacted therewith, so that at least the quantity required for reaction is still present, and treating the fibers or sheet materials containing the remainder of the aqueous alkaline reaction mixture with heat energy. This patent also relates to equipment for performing the process.

Carboxymethyl cellulose (CMC) fibers are manufactured by reacting a starting cellulose with an alkaline solution containing an etherifying agent dissolved therein while the cellulose is filled in a reactor and the solution is circulating by a pump so as to come into continuous contact with the cellulose, according to U.S. Pat. No. 4,410,694.

It would be desirable to find alternative methods for converting cellulose into simple sugars, such as glucose, particularly if those methods were cost effective and/or could be implemented in continuous or other large scale processes.

SUMMARY

There is provided, in one non-limiting form, a method for converting cellulose into simple sugars comprising, in the presence of water, contacting cellulose with a compound effective to catalytically cleave the ether bonds of the cellulose to give at least one simple sugar, where the additive is selected from the group consisting of vitamins, compounds with at least one ylide functionality, porphyrins, flavins, pyridoxal-containing molecules, and combinations thereof.

In one non-limiting embodiment, the cellulose is carboxymethyl cellulose (CMC) made by a method comprising reacting crystalline cellulose with chloroacetic acid and a base selected from the group consisting of sodium hydroxide, potassium hydroxide, ammonium hydroxide and mixtures thereof.

DETAILED DESCRIPTION

Figure 1:
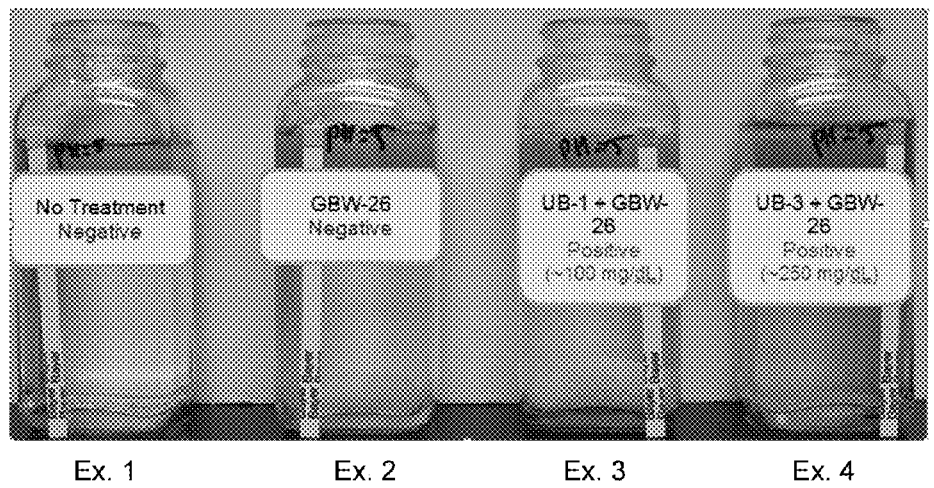
FIG. 1 is a photograph of four bottles of mixtures, one of which is a control and the others showing CMC breakdown with an enzyme breaker alone or together with vitamins UB-1 and UB-3 under acidic conditions (pH=5.0)

It has been discovered that vitamins B1, B2 and/or B12, other porphyrins flavins, pyridoxal-containing molecules, and other chemical compounds with an ylide functional group can catalytically cleave the ether bonds of cellulose in water to produce free glucose.

In more detail, the cellulose may be from any suitable source, and may be carboxymethyl cellulose (CMC) in one non-limiting embodiment. In another non-restrictive version, the CMC may be made by a method that includes, but is not necessarily limited to, reacting crystalline cellulose with chloroacetic acid and a base. Suitable cellulosic starting materials include, but are not necessarily limited to, wood (from which the lignin has been removed), sugar beets, bagasse, sago waste, corn stover, olive pits, cane, miscanthus, duckweed, and the like. It is expected that grasses would be easier to process than trees because they have less lignin. Suitable bases include, but are not necessarily limited to, sodium hydroxide, potassium hydroxide, ammonium hydroxide and mixtures thereof. This method breaks up the crystalline nature of the cellulose, making it more water soluble and thus available for the hydrolysis of the method further described herein. Elevated temperatures (above room temperature, defined herein as about 70° F. or about 21° C.), and mixing help the production of CMC. Alternatively, adding about 60 to about 90 wt % ethanol to the water makes the cellulose more dispersible and improves the reaction. Without being limited to any particular mechanism or explanation, it is believed that making the cellulose more water-soluble may enhance the ability of the ylide functional group-containing compounds to work.

Suitable catalytic compounds include those containing at least one ylide functional group which include, but are not necessarily limited to, vitamins such as B1, ylides containing phosphorous (phosphonium ylides), ylides containing sulfur (sulfonium ylides, sulfoxonium ylides), ylides containing oxygen (carbonyl ylides, oxonium ylides), ylides containing nitrogen (asomethine ylides, iminium ylides), halogen-containing ylides (halonium ylides), and combinations thereof. Compounds that are porphyrins, such as B12 and those having similar molecular structures are also expected to be useful catalysts. Suitable vitamins include, but are not necessarily limited to, B1, B2, B6, B12, and combinations thereof. In one non-limiting embodiment, these vitamins are in their ylide form. Suitable catalytic compounds also include, but are not necessarily limited to, flavins and pyridoxal-containing molecules; more specifically in another non-restrictive version, these include flavins, riboflavin, flavin mononucleotide (FMN) and flavin adenine dinucleotide (FAD), and pyridoxal phosphate, pyridoxl and pyridoxamines.

An ylide is defined herein a neutral dipolar molecule containing a formally negatively charged atom (usually a carbanion) directly attached to a hetero atom with a formal positive charge (usually nitrogen, phosphorous or sulfur) and in which both atoms have full octets of electrons. Ylides are thus 1,2-dipolar compounds.

An enzyme breaker may be used together with the catalyst. Suitable enzyme breakers include, but are not necessarily limited to, cellulases, alpha-mannanases, beta-mannanases, galactosidases, glucosidases, amylases, hemicellulases, glycosylases, and combinations thereof. The proportion of enzyme breakers, based on the amount of cellulose, may range from about 1 ng/mL independently to about 1 µg/mL; alternatively from about 0.5 ng/mL independently to about 1 mg/mL. Alternatively, the enzyme concentration may be represented by the dilution rate. For example: the enzyme is diluted to a concentration of about 1:200 and is present in the fluid in a range of about 0.25-5 gpt. Alternatively, the enzyme can be diluted to a concentration of 1:25 and is present in the fluid in a range of about 0.25 to 10 gpt.

Water should be present in the mixture of the cellulose and the catalytic compound. The catalytic compound is present in an amount ranging from about 0.005 wt % independently to about 1 wt %, based on the cellulose present; alternatively from about 0.01 wt % independently to about 1 wt %, based on the cellulose present. As used herein in connection with a range, the word "independently" means that any lower threshold may be used together with any upper threshold to give a suitable alternative range.

It may also be desirable to bind the catalytic compound to a heterogeneous substrate so that these catalysts may be easily separated from the resulting aqueous sugar solution. That is, in one non-limiting embodiment, the heterogeneous substrate is solid. This would permit re-use of the catalyst compound containing at least one ylide functional group. Suitable substrates include, but are not necessarily limited to, inorganic materials such as clay, sand, plastic beads, such as polystyrene, various resins such as polystyrenics used in ion exchange resins, and even metal supports, similar to those used as packing materials used in contactors and distillation towers. In some non-limiting versions, the pH of the resulting sugar solution may be adjusted to precipitate the vitamins or other catalysts so that the sugars can be purified. That is, if the aqueous mixture is acidic, the pH is adjusted with a base as a neutralizer, such as lime; and if the aqueous mixture is basic, the pH is adjusted with an acid as a neutralizer. For instance, if phosphoric acid is used to lower pH to within the range given below, then lime may be used as a neutralizer to precipitate calcium phosphate in the recovery step.

It has been further discovered that the catalytic cleaving of the ether groups of the cellulose with the compound may be performed under acidic or alkaline conditions. In one non-limiting embodiment, the alkaline pH of the mixture may range from about 8 independently to about 12; alternatively from about 9 independently to about 10. Suitable bases to adjust the pH to within these basic ranges include, but are not necessarily limited to, sodium hydroxide, potassium hydroxide, ammonium hydroxide, and the like, and mixtures thereof. In a different, non-restrictive version, an acidic range may be from about 5 independently to about 7 pH; alternatively from about 6 independently to about 7 pH. Suitable acids for adjusting the pH of the reaction mixture include, but are not necessarily limited to, sulfuric acid, citric acid, acetic acid, hydrochloric acid, phosphoric acid, and the like and mixtures thereof.

The catalytic conversion of cellulose to simple sugars (e.g. glucose), may also be advantageously done at about room temperature (70° F.; 21° C.) or at elevated temperature, above room temperature, independently up to about 350° F. (about 177° C.). Alternatively, the temperature may range from about 150° F. (about 66° C.) independently to about 250° F. (about 121° C.). In most cases, it appears that elevated temperatures (above room temperature) speed up the cellulose breakdown process. A pressure vessel may be required to reach these elevated temperatures.

The following examples are illustrative of some of the embodiments of the present invention, which examples are not intended to limit the invention, but are provided to further illustrate it.

All percentages set forth in the Examples are given in terms of weight units except as may otherwise be indicated.

EXAMPLES

Cellulose breakdown with universal breakers (UB-1 and UB-3) were performed under both acidic and alkaline conditions (pH=5.0 and 10.0, respectively) and with temperature of 150° F. and 175° F., respectively (66° C. and 79° C., respectively) for approximately 21-24 hours. Microcrystalline cellulose and carboxymethyl cellulose (CMC) were used.

Forty pounds (about 18 kg) of CMC was prepared, mixed for 30 minutes, and adjusted to pH=5.00 and pH=10.02, respectively, to observe the efficacy of cellulose breakdown under acidic and alkaline conditions. Thirty gallons per thousand (30 gpt; same value for any SI units, e.g. 30 liters per thousand liters) of UB-1 and UB-3 and 5 gpt of enzyme breaker GBW-26C) were used. GBW-26C is a cellulose enzyme breaker available from Baker Hughes, Inc. UB-1 and UB-3 were as noted in Table I:

TABLE I

| Breaker | Composition |
|---------|-------------|
| UB-1 | Vitamin B1 |
| UB-3 | Vitamin B12 |

Figure 2:
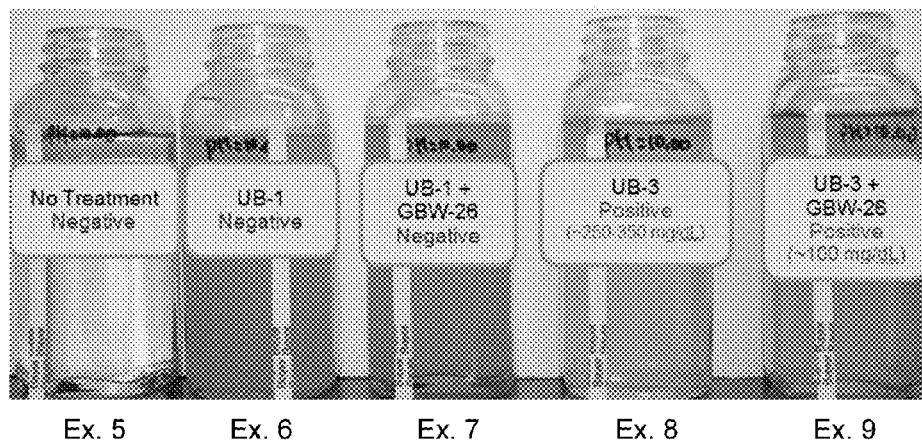
FIG. 2 is a photograph of five bottles of mixtures, one of which is a control and the others showing CMC breakdown with vitamins UB-1 and UB-3 under alkaline conditions (pH=10.0).

After 21 hours incubation at 150° F. (66° C.), the presence of glucose was observed when CMC was treated with UB-1 and UB-3 (FIGS. 1 and 2). FIG. 1 showed that UB-1 and UB-3 could break CMC under acidic conditions when GBW-26C was added.

More specifically, the photo in FIG. 1 showed that the results in Example 2 (GBW-26C enzyme breaker alone) gave negative results: it is visually indistinguishable from Example 1, the control which had no treatment. However, the use of both UB-1 and GBW-26C were effective at catalytic breakdown and gave approximately 100 mg/dL glucose (Example 3). Additionally, the use of UB-3 and GBW-26C in Example 4 also gave a positive result, about 250 mg/dL glucose and a pink color (which shows as light gray in the grayscale of FIG. 4).

Results in the photograph of FIG. 2 showed that UB-3 was effective in breaking CMC under alkaline conditions (Examples 8 and 9) compared to UB-1 (Examples 6 and 7, respectively), without the addition of enzyme breaker, GBW-26C. UB-1 was not effective in breaking CMC under alkaline conditions (Examples 6 and 7). The contents of the bottles for Examples 6 and 7 were light gray compared to the control of Example 5, whereas the contents of the bottles for Examples 8 and 9 were a light pink.

DIASTIX® reagent glucose test strips (catalog # AM 2803 available from Bayer) were used to test for the presence of glucose in treated samples with UB-1 and UB-3. The glucose concentrations noted in FIGS. 1 and 2 were approximate concentrations based on color changes on DIASTIX test strips.

In the foregoing specification, the invention has been described with reference to specific embodiments thereof, and has been demonstrated as effective in providing methods and compositions for catalytically breaking down cellulose into glucose using various catalysts such as vitamins, porphyrins flavins, pyridoxal-containing molecules, and compounds having ylide functionality. While it will be appreciated that the methods and compositions described herein will find particular application and use in catalytically breaking down CMC, the methods and catalysts will likely find utility in cleaving other celluloses into simple sugars as well. However, it will be evident that various modifications and changes can be made thereto without departing from the broader spirit or scope of the invention as set forth in the appended claims. Accordingly, the specification is to be regarded in an illustrative rather than a restrictive sense. For example, specific combinations of celluloses, catalysts, substrates, acids, bases, and reaction conditions falling within the claimed parameters, but not specifically identified or tried in a particular method or composition, are anticipated to be within the scope of this invention. Furthermore, reaction conditions other than those specifically exemplified herein are expected to be useful for the methods described herein.

The terms "comprises" and "comprising" used in the claims herein should be interpreted to mean including, but not limited to, the recited elements.

The present invention may suitably comprise, consist or consist essentially of the elements disclosed and may be practiced in the absence of an element not disclosed. For instance, the method of converting cellulose into simple sugars may consist of or consist essentially of, contacting cellulose with a compound in the presence of water catalytically cleaving the ether bonds of the cellulose to give at least one simple sugar, where the compound is selected from the group consisting of vitamins, compounds with at least one ylide functionality, porphyrins, flavins, pyridoxal-containing molecules, and combinations thereof.

What is claimed is:

1. A method of converting cellulose into simple sugars comprising:
    in the presence of water, contacting cellulose with an enzyme breaker and vitamin B1 effective to catalytically cleave ether bonds of the cellulose to give at least one simple sugar;
    where contacting the cellulose, the enzyme breaker, and the vitamin B1 occurs in an aqueous mixture having a pH in the alkaline range of from about 8 to about 12.

2. The method of claim 1 where the cellulose is carboxymethyl cellulose (CMC) made by a method comprising reacting crystalline cellulose with chloroacetic acid and a base selected from the group consisting of sodium hydroxide, potassium hydroxide, ammonium hydroxide and mixtures thereof.

3. The method of claim 1 where the vitamin B1 is bound to a heterogeneous substrate and the method further comprises removing the compound from the at least one simple sugar.

4. The method of claim 3 where the substrate is selected from the group consisting of clays, sand, plastic beads, resins, metals, and combinations thereof.

5. The method of claim 1 further comprising adjusting the pH to be within the alkaline range using a base selected from the group consisting of sodium hydroxide, potassium hydroxide, ammonium hydroxide and mixtures thereof.

6. The method of claim 1 where the contacting occurs at a temperature between about 70 to about 350° F.

7. A method of converting cellulose into simple sugars comprising:
    in the presence of water, contacting cellulose with an enzyme breaker and vitamin B1 effective to catalytically cleave ether bonds of the cellulose to give at least one simple sugar, where the compound is present in an amount ranging from about 0.005 wt % to about 1 wt %, based on the cellulose present;
    where contacting the cellulose, the enzyme breaker, and the vitamin B1 occurs in an aqueous mixture having a pH in the alkaline range of from about 8 to about 12.

8. The method of claim 7 where the cellulose is carboxymethyl cellulose (CMC) made by a method comprising reacting crystalline cellulose with chloroacetic acid and a base selected from the group consisting of sodium hydroxide, potassium hydroxide, ammonium hydroxide and mixtures thereof.

9. The method of claim 7 where the vitamin B1 is bound to a heterogeneous substrate and the method further comprises removing the compound from the at least one simple sugar.

10. The method of claim 7 where the contacting occurs at a temperature between about 70 to about 350° F.

11. A method of converting cellulose into simple sugars comprising:
    in the presence of water, contacting cellulose with an enzyme breaker and vitamin B1 effective to catalytically cleave ether bonds of the cellulose to give at least one simple sugar, where the cellulose is carboxymethyl cellulose (CMC) made by a method comprising reacting crystalline cellulose with chloroacetic acid and a base selected from the group consisting of sodium hydroxide, potassium hydroxide, ammonium hydroxide and mixtures thereof, and where the contacting occurs at a temperature between about 70 to about 350° F.;

where contacting the cellulose, the enzyme breaker, and the vitamin B1 occurs in an aqueous mixture having a pH in the alkaline range of from about 8 to about 12.

12. The method of claim 11 where the vitamin B1 is bound to a heterogeneous substrate and the method further comprises removing the compound from the at least one simple sugar.

13. The method of claim 11 where the vitamin B1 is present in an amount ranging from about 0.005 wt % to about 1 wt %, based on the cellulose present.

14. The method of claim 1 where the enzyme breaker is selected from the group consisting of cellulases, alpha-mannanases, beta-mannanases, galactosidases, glucosidases, amylases, hemicellulases, glycosylases, and combinations thereof.

15. The method of claim 1 where the enzyme breaker is a cellulose enzyme breaker.

16. The method of claim 7 where the enzyme breaker is selected from the group consisting of cellulases, alpha-mannanases, beta-mannanases, galactosidases, glucosidases, amylases, hemicellulases, glycosylases, and combinations thereof.

17. The method of claim 11 where the enzyme breaker is selected from the group consisting of cellulases, alpha-mannanases, beta-mannanases, galactosidases, glucosidases, amylases, hemicellulases, glycosylases, and combinations thereof.

* * * * *